(12) United States Patent
Hopper et al.

(10) Patent No.: US 8,103,343 B2
(45) Date of Patent: Jan. 24, 2012

(54) AUTOMATIC MODULATION OF PACING TIMING INTERVALS USING BEAT TO BEAT MEASURES

(75) Inventors: Donald L. Hopper, Maple Grove, MN (US); Yinghong Yu, Shoreview, MN (US); Allan Charles Shuros, St. Paul, MN (US); Shantha Arcot-Krishnamurthy, Roseville, MN (US); Gerrard M. Carlson, Champlin, MN (US); Jeffrey Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 501 days.

(21) Appl. No.: 11/799,794

(22) Filed: May 3, 2007

(65) Prior Publication Data

US 2008/0275520 A1 Nov. 6, 2008

(51) Int. Cl.
*A61N 1/362* (2006.01)
(52) U.S. Cl. .......................................................... 607/9
(58) Field of Classification Search ................... 607/9, 2, 607/45, 25, 7, 11, 17, 27; 600/510, 513, 600/509
See application file for complete search history.

(56) References Cited

U.S. PATENT DOCUMENTS

| | | |
|---|---|---|
| 4,674,518 A | 6/1987 | Salo |
| 4,686,987 A | 8/1987 | Salo |
| 5,334,222 A | 8/1994 | Salo |
| 5,417,717 A | 5/1995 | Salo |
| 5,466,245 A | 11/1995 | Spinelli |
| 5,487,752 A | 1/1996 | Salo et al. |
| 5,601,613 A | 2/1997 | Florio et al. |
| 5,626,623 A | 5/1997 | Kieval et al. |
| 5,700,417 A | 12/1997 | Fernyhough |
| 5,800,464 A * | 9/1998 | Kieval ............................... 607/9 |
| 6,141,590 A | 10/2000 | Renirie |
| 6,144,800 A | 11/2000 | Kobayashi |
| 6,144,880 A | 11/2000 | Ding et al. |
| 6,221,011 B1 | 4/2001 | Bardy |
| 6,270,457 B1 | 8/2001 | Bardy |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,371,922 B1 | 4/2002 | Baumann |
| 6,398,728 B1 | 6/2002 | Bardy |
| 6,440,066 B1 | 8/2002 | Bardy |
| 6,640,135 B1 | 10/2003 | Salo et al. |
| 6,748,271 B2 | 6/2004 | Spinelli et al. |

(Continued)

OTHER PUBLICATIONS

Tacker Willis A, and Geddes Leslie A. "The Laws of Electrical Stimulation of Cardiac Tissue." Proceedings of the IEEE, vol. 84. No. 3, Mar. 1996.*
U.S. Appl. No. 11/894,081, filed Aug. 20, 2007, Maskara et al.
Office Action dated May 12, 2010 for U.S. Appl. No. 11/894,082, 16 pages.
International Preliminary Report on Patentability dated Mar. 4, 2010 from International Application No. PCT/US2008/009612, 10 pages.

(Continued)

*Primary Examiner* — Carl H Layno
*Assistant Examiner* — Paula J Stice
(74) *Attorney, Agent, or Firm* — Hollingsworth & Funk, LLC

(57) ABSTRACT

Methods and systems to modulate timing intervals for pacing therapy are described. For each cardiac cycle, one or both of an atrioventricular (A-V) timing interval and an atrial (A-A) timing interval are modulated to oppose beat-to-beat ventricular (V-V) timing variability. Pacing therapy is delivered using the modulated timing intervals.

18 Claims, 10 Drawing Sheets

U.S. PATENT DOCUMENTS

| | | | |
|---|---|---|---|
| 6,871,088 B2 * | 3/2005 | Chinchoy | 600/510 |
| 6,985,772 B2 | 1/2006 | Holmstrom et al. | |
| 7,027,866 B2 | 4/2006 | Warkentin | |
| 7,107,093 B2 * | 9/2006 | Burnes | 600/509 |
| 7,181,285 B2 | 2/2007 | Lindh | |
| 7,221,979 B2 * | 5/2007 | Zhou et al. | 607/44 |
| 7,302,295 B2 * | 11/2007 | Stahmann et al. | 607/20 |
| 7,930,027 B2 | 4/2011 | Prakash et al. | |
| 2002/0082646 A1 * | 6/2002 | Casavant et al. | 607/9 |
| 2003/0040777 A1 * | 2/2003 | Shemer et al. | 607/9 |
| 2004/0024421 A1 * | 2/2004 | Ideker et al. | 607/9 |
| 2004/0127804 A1 * | 7/2004 | Hatlesad et al. | 600/513 |
| 2005/0027323 A1 | 2/2005 | Mulligan et al. | |
| 2005/0038479 A1 * | 2/2005 | Deno et al. | 607/9 |
| 2005/0043764 A1 * | 2/2005 | Wesselink et al. | 607/9 |
| 2005/0109338 A1 | 5/2005 | Stahmann | |
| 2005/0234517 A1 * | 10/2005 | Braunschweig et al. | 607/6 |
| 2006/0173493 A1 * | 8/2006 | Armstrong et al. | 607/2 |
| 2006/0247702 A1 | 11/2006 | Stegemann et al. | |
| 2007/0060959 A1 | 3/2007 | Salo et al. | |
| 2007/0293897 A1 * | 12/2007 | Sheldon et al. | 607/9 |
| 2008/0269816 A1 * | 10/2008 | Prakash et al. | 607/9 |

OTHER PUBLICATIONS

International Search Report and Written Opinion dated Nov. 17, 2008 from International Application No. PCT/US2008/009612, 15 pages.
Restriction dated Mar. 22, 2010 from U.S. Appl. No. 11/894,082, 7 pages.
Restriction Response submitted Apr. 21, 2010 to Restriction dated Mar. 22, 2010 from U.S. Appl. No. 11/894,082, 5 pages.
Nakamoto et al., "Variability of Ventricular Excitation Interval Does Not Reflect Fluctuation in Atrial Excitation Interval during Exercise in Humans: AV Nodal Function as Stabilizer", J. Physiol. Sci., vol. 56, No. 1, Feb. 2006, pp. 67-77.
Ogoh et al., "Cardiopulmonary Baroreflex is Reset During Dynamic Exercise", J. Appl Physiol, 100, 2006, pp. 51-59.
Nakamoto et al., "Beat-to-Beat Modulation of Atrioventricular Conduction during Dynamic Exercise in Humans", Japanese Journal of Physiology, vol. 55, 2005, pp. 37-51.
File History for U.S. Appl. No. 11/894,081.
Office Action dated Jan. 24, 2011 from Australian Application No. 2008289617, 5 pages.
File History for U.S. Appl. No. 11/894,082.

* cited by examiner

AUTOMATIC MODULATION OF PACING TIMING INTERVALS USING BEAT TO BEAT MEASURES

FIELD OF THE INVENTION

The present invention relates generally to cardiac pacing therapy, and more specifically, to automatic adjustment of pacing intervals.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrioventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and for delivering stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). HF causes diminished pumping power of the heart, resulting in the inability to deliver enough blood to meet the demands of peripheral tissues. HF may cause weakness, loss of breath, and build up of fluids in the lungs and other body tissues. HF may affect the left heart, right heart or both sides of the heart. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dysynchrony. Particularly when the left or right ventricles are affected, the unsynchronized contractions can significantly decrease the pumping efficiency of the heart.

Pacing therapy to promote synchronization of heart chamber contractions to improve cardiac function is generally referred to as cardiac resynchronization therapy (CRT). Some cardiac pacemakers are capable of delivering CRT by pacing multiple heart chambers. Pacing pulses are delivered to the heart chambers in a sequence that causes the heart chambers to contract in synchrony, increasing the pumping power of the heart and delivering more blood to the peripheral tissues of the body. In the case of dysynchrony of right and left ventricular contractions, a biventricular pacing therapy may pace one or both ventricles. Bi-atrial pacing or pacing of all four heart chambers may alternatively be used.

SUMMARY OF THE INVENTION

The present invention is directed to systems and methods for automatic adjustment of pacing intervals. One embodiment is directed to a method for delivering pacing therapy to a heart. For each cardiac cycle, one or both of an atrioventricular (A-V) timing interval and an atrial (A-A) timing interval are modulated to oppose beat-to-beat ventricular (V-V) timing variability. Pacing therapy is delivered using the modulated timing intervals.

In some implementations, a sensor indicated pacing rate may be determined based on the patient's physiological status and the timing intervals of the indicated pacing rate may be modulated to oppose beat-to-beat ventricular (V-V) timing variability. Physiological status is determined, for example, by sensing metabolic need, autonomic tone and/or hemodynamic status.

In addition to modulating the A-V and A-A intervals, one or more of an interventricular delay interval, an intraventricular delay interval, an interatrial delay interval, or an intraatrial delay interval may also be modulated to improve cardiac function.

Modulation of the timing intervals may be effected to produce optimal stroke volume for each beat. As the base pacing rate is varied to produce physiologic respiratory sinus arrhythmia, the timing intervals may also be modulated based on respiration. An amount or degree of the modulation may be a function of exertion level or heart rate. Independent modulation of the timing intervals may be based on one or more parameters that affect heart function. The parameters may include, for example, one or more of stroke volume, blood pressure, blood flow, cardiac contractility, baroreflex, chemoreflex and/or other parameters.

One implementation involves sensing a physiological parameter of a right heart chamber during a cardiac cycle. The timing intervals are independently modulated for a next cardiac cycle based on the sensed right heart chamber parameter.

The timing intervals can be initially determined using an algorithm designed to optimize the pacing intervals for a particular type of disorder experienced by the patient, such as heart failure. For example, modulating the timing intervals may involve modulating an atrioventricular interval and/or interventricular delay interval and/or other timing intervals to provide cardiac resynchronization therapy.

Another embodiment of the invention is directed to a cardiac rhythm management device. The device includes a sensor system configured to sense one or more physiological parameters. For each cardiac cycle, a therapy control processor independently modulates one or more of atrial (A-A) timing interval and an atrioventricular (A-V) timing interval to oppose ventricular (V-V) timing variability based on the sensed physiological parameters. A therapy delivery system delivers pacing to the heart using the independently modulated timing intervals. The sensor system may include, for example, a respiration sensor and the therapy control processor may control deliver of pacing based on respiration cycle phase to mimic natural respiratory sinus arrhythmia. Modulation of the pacing timing intervals may also occur based on respiration cycle phase.

According to one aspect, the therapy control processor is configured to modulate the A-A and A-V timing intervals to cancel fluctuations in the V-V intervals within one beat at elevated heart rates. In addition, the therapy control processor may be further configured to modulate one or more of an interventricular timing interval, an intraventricular timing interval, an interatrial timing interval, and an intraatrial timing interval.

In one implementation, the sensor system is configured to sense a physiological parameter of a right heart chamber during a cardiac cycle. The therapy control processor independently modulates the timing intervals of the indicated pacing rate for a next cardiac cycle based on the sensed right heart chamber parameter. Rate dependent modulation of the pacing timing intervals may be used to produce optimal stroke volume for each cardiac beat at elevated heart rates.

In certain configurations, the therapy control processor is configured to control delivery of non-excitory electrical stimulation to alter myocardial contractility. The therapy delivery system is configured to deliver the non-excitory electrical stimulation under control of the therapy control processor.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
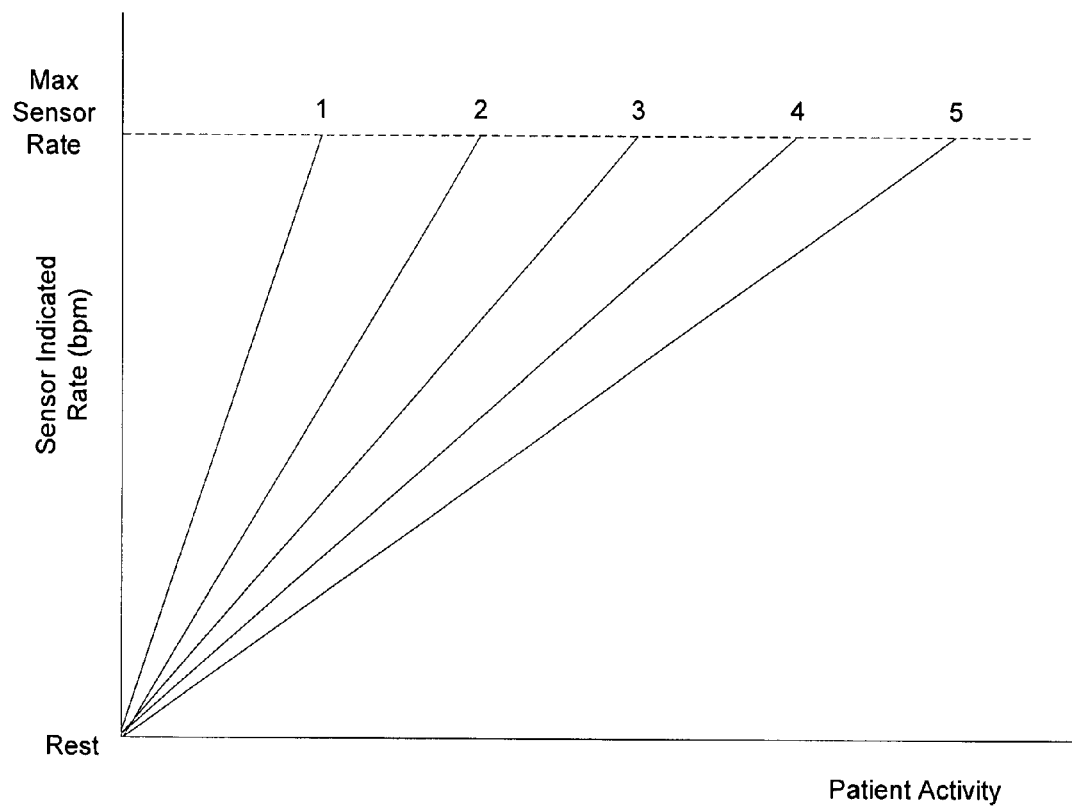
FIG. 1A illustrates graphs of the sensor indicated rate as a function of patient activity.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Recent studies show that during exercise the intrinsic variability of the P-P and R-R intervals decreases, with the decrease in the variability of the R-R being most pronounced, especially at higher heart rates of about 140-160 bpm. Conversely, variability of the P-R interval and the change in P-R interval variability increases during exercise. The conclusion drawn from these studies is that at elevated heart rates the AV nodal mechanism functions to produce P-R intervals that cancel fluctuations in the P-P intervals within one beat and to decrease the variability of R-R intervals. (See e.g., "Variability of Ventricular Excitation Interval does not Reflect Fluctuation in Atrial Excitation Interval during Exercise in Humans: AV Nodal Function as Stabilizer," J. Physiol. Sci. Vol. 56, No. 1, February 2006, pp. 67-77).

As exertion increases from a resting level, stroke volume typically increases and then gradually plateaus. Stroke volume is increased through a number of mechanisms, including increased ventricular preload, decreased ventricular afterload, and increased myocardial contractility. At high levels of exertion, stroke volume remains relatively constant and additional cardiac output is achieved through increased heart rate.

The intrinsic variability of the P-R intervals operates to stabilize beat to beat stroke volume. For example, if stroke volume decreases as a result of decreased preload, the AV node operates to elongate the P-R interval and shorten the P-P interval whereas if stroke volume increases due to increased preload, the P-R interval is shortened and the P-P interval is elongated. This effect is especially pronounced during ventilation cycles.

Embodiments of the invention are directed to systems and methods to produce beat to beat modulation of atrial, ventricular, and/or atrioventricular pacing timing intervals to produce physiologic pacing that provides optimal stroke volume. The approaches described herein provide for modulation of one or more pacing timing intervals for each cardiac cycle, where the atrioventricular (AV) timing interval and/or atrial (A-A) timing interval are modulated to oppose ventricular (V-V) timing variability. The approaches of the invention involve adjusting the timing intervals between one or more of a sensed or paced atrial beat of a cardiac cycle and a paced atrial beat for the next cardiac cycle, a sensed or paced ventricular beat of a cardiac cycle and a paced ventricular beat of the next cardiac cycle, a sensed or paced atrial beat of a cardiac cycle and a paced ventricular beat of the cardiac cycle, an interventricular interval between two ventricular beats of a cardiac cycle, and an interatrial interval between two atrial beats of a cardiac cycle.

In embodiments described herein, a cardiac rhythm management device, such as an implantable pacemaker or pacemaker/defibrillator, provides rate dependent modulation of pacing timing intervals beat by beat to achieve optimal stroke volume and decreased variability between ventricular beats to mimic the observed physiologic response discussed above. Beat to beat modulation of the pacing timing intervals may be performed automatically by the device based on measures of one or more physiological parameters, including parameters such as, stroke volume, cardiac output, total peripheral resistance, blood pressure, baroreflex, chemoreflex, cardiac contractility, and/or other measured parameters.

Modulation of the pacing timing intervals in accordance with the embodiments described herein may be superimposed on a pacing rate indicated by rate adaptive pacing and/or to achieve respiration sinus arrhythmia (RSA) or heart rate variability (HRV). Rate adaptive pacing has previously been accomplished by adjusting the pacing rate in response to changes in the sensed physical activity. The pacing rate calculated for the level of sensed physical activity is typically referred to as the sensor indicated rate or SIR. FIG. 1A illustrates graphs of the sensor indicated rate as a function of patient activity. In this example, pacing gains of 1-5 may be selected by the user to vary the slope of the SIR graphs. The sensor used to determine the sensor indicated rate typically may be an accelerometer (or other motion sensor) or a minute ventilation (MV) sensor.

Figure 1B:
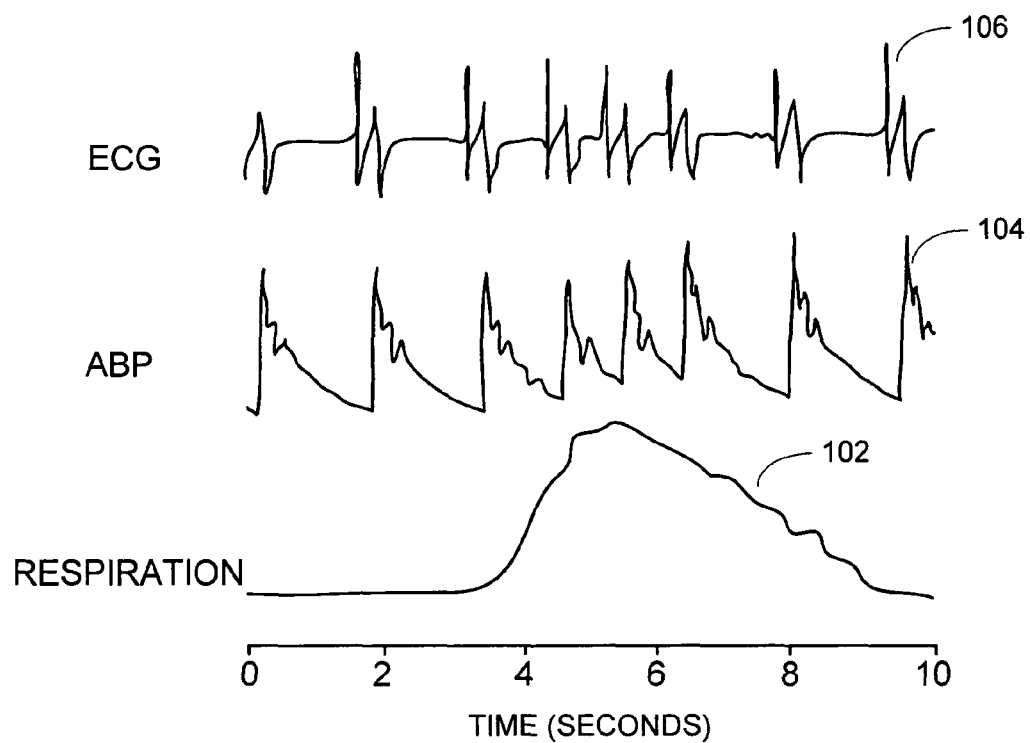
FIG. 1B is a graph comparing respiration, blood pressure, and heart rate in a healthy individual.

Additionally, or alternatively, the pacing rate may be varied to mimic natural variability of the heart rate (HRV). Under healthy conditions, heart rate and blood pressure vary with respiration. The heart rate varies in response to autonomic as well as other regulatory inputs to the sinoatrial node (SA). FIG. 1B is a graph comparing a respiration signal 102, blood pressure signal 104, and electrocardiogram (ECG) 106 in a healthy individual. PR and RR intervals shorten during ventilation and this modulation of heart rate with respiration is known as respiratory sinus arrhythmia (RSA). The rate variations of RSA have been found to be important to survival. Individuals without RSA have higher rates of overall mortality when compared to those with RSA.

Figure 2A:
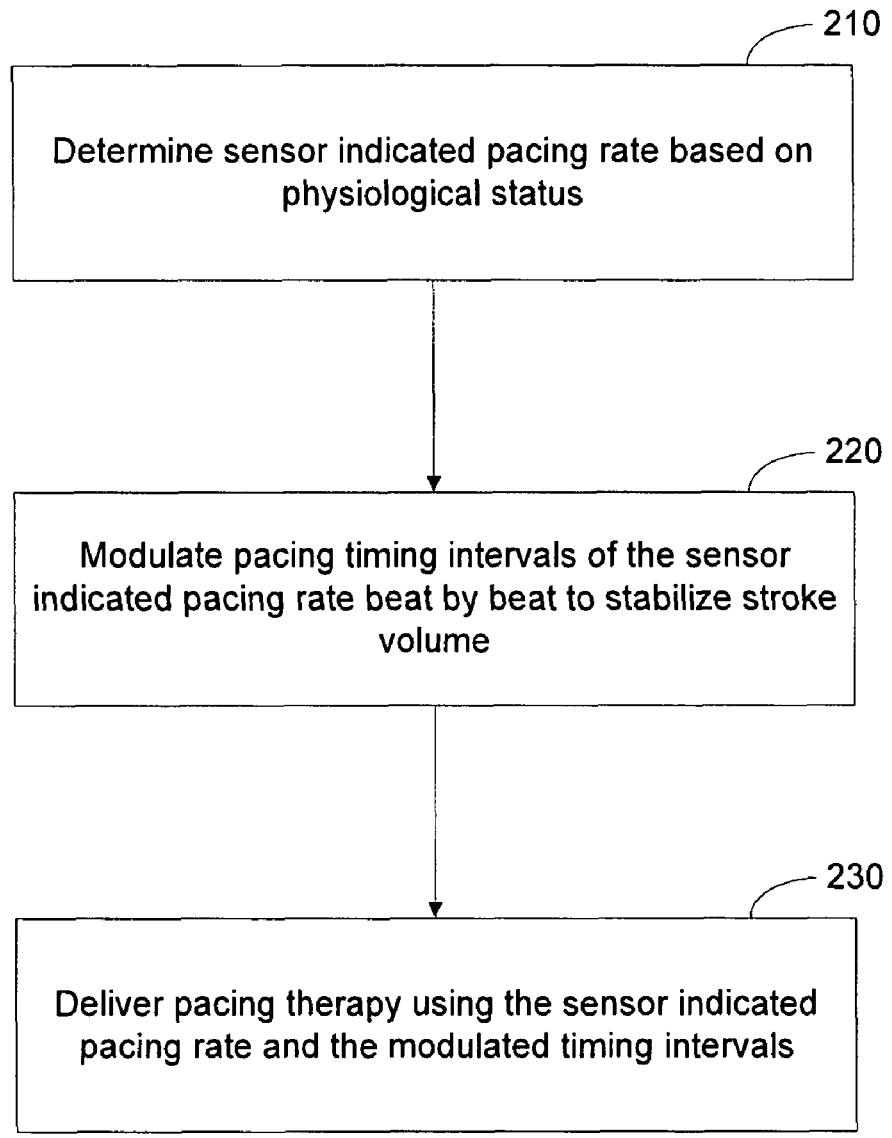
FIG. 2A is a flow diagram illustrating a method for modulating timing intervals in accordance with embodiments of the invention.

Embodiments of the present invention involve pacing at a rate sufficient to meet the metabolic demand for the patient's activity level and also introducing rate dependent variability in the pacing timing intervals which serves to stabilize stroke volume beat to beat at elevated heart rates. FIG. 2A is a flow diagram illustrating a method for modulating pacing timing intervals in accordance with embodiments of the invention. A SIR for rate adaptive pacing is determined 210 based on the patient's physiologic state. For example, determining the physiological state may involve determining the patient's metabolic demand based on hemodynamics or respiration over one or more previous beats. The degree of modulation of the pacing intervals may also be a function of metabolic demand with modulation increasing with exertion and/or heart rate. In some embodiments, metabolic demand is determined through the use of a patient activity sensor, such as an accelerometer and/or minute ventilation (MV) sensor which is configured to detect the level of patient activity. The SIR is determined based on the output of the patient activity sensor.

The pacing timing intervals of the sensor indicated pacing rate are modulated beat by beat 220 for each cardiac cycle to maintain an optimal stroke volume. Stroke volume is limited by the amount of blood entering the ventricle from the atrium between ventricular contractions and may be increased through various mechanisms including increased ventricular preload and decreased afterload. The pacing timing intervals may be modulated to achieve a stroke volume for each cardiac cycle that provides optimal cardiac output. An approach of the invention involves introducing rate dependent variability into the A-A intervals and the A-V intervals so that variations of the A-A intervals are compensated for by variations in the A-V intervals to maintain V-V intervals relatively constant at higher heart rates. Pacing therapy is delivered 230 using the sensor indicated pacing rate and the modulated timing intervals.

Figure 2B:
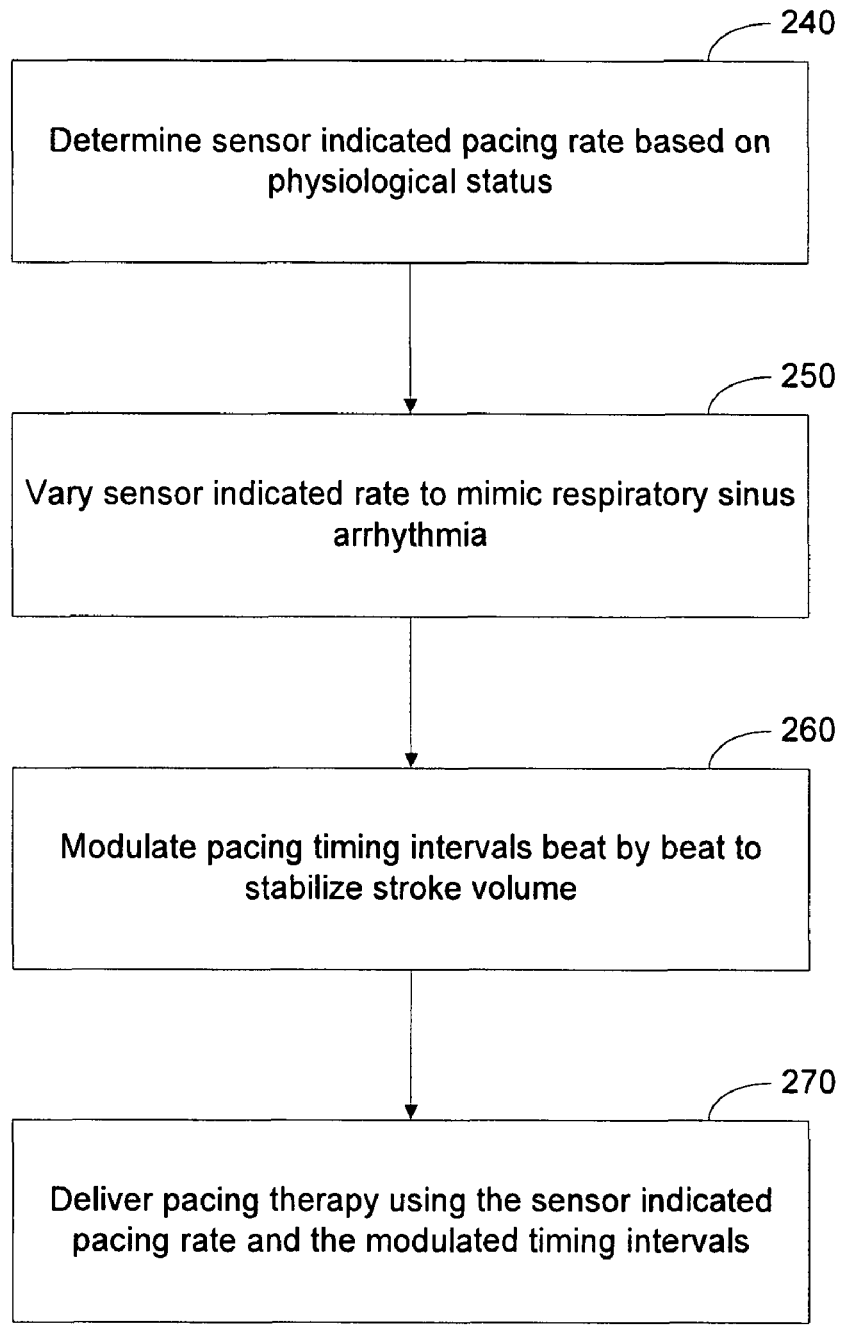
FIG. 2B is a flow diagram that illustrates a method for pacing interval modulation that includes variation based on RSA in accordance with embodiments of the invention.

In certain embodiments, the approaches of the invention may involve varying the SIR and/or modulating the pacing timing intervals with respiration cycle phase to achieve a heart rate that mimics natural RSA. Modulation of the pacing timing intervals to produce the optimal stroke volume beat by beat is superimposed on the SIR with variations for RSA and may also take into account respiratory cycle phase. The flow diagram of FIG. 2B illustrates a method for pacing interval modulation that includes variation based on RSA. A sensor indicated rate is determined 240 based on patient activity. The sensor indicated pacing rate is varied 250 based on respiration cycle phase to mimic respiratory sinus arrhythmia. Pacing intervals of SIR varied to mimic RSA are varied 260 to provide optimal beat to beat stroke volume. Therapy is delivered 270 using the indicated pacing rate varied for RSA and the modulated pacing timing intervals.

Various techniques have been used to determine pacing timing intervals that increase cardiac pumping efficiency for patients suffering from various disorders that prevent the heart from operating normally. For example, one such disorder involves degeneration of the LV conduction system, blocking propagation of electrical signals through the specialized conduction pathways of the heart and causing contraction of the LV to occur in stages rather than synchronously. Another disorder of the heart occurs when blood in the LV flows backward to the LA resulting in reduced stroke volume and cardiac output. Both of these disorders may be found separately or in combination in patients exhibiting congestive heart failure (CHF). Patients suffering from these disorders benefit from pacing that improves contractility and/or stroke volume. Embodiments of the invention may modulate pacing timing intervals for A-V, interventricular delay (IVD) and/or interatrial delay (IAD) to treat CHF and related disorders. Timing intervals between paces delivered to multiple electrodes disposed within a single cardiac chamber, denoted intraventricular timing intervals or intraatrial timing intervals, may alternatively or additionally be modulated. Initial pacing timing intervals for A-V, IVD, IAD, and/or intrachamber timing intervals may be initially determined using various techniques such as those described in the following commonly owned U.S. Pat. Nos. 6,144,880, 7,181,285, 5,466,245, 5,700,417, 5,334,222, and 6,371,922 which are incorporated herein by reference. Following determination of initial values for one or more of these timing intervals, modulation of the timing intervals around the initial values may be applied using the approaches of the present invention. For example, an initial AV interval delay determined as optimal from one of the techniques described in the above referenced patents may be modulated beat by beat to achieve optimal stroke volume.

Figure 2C:
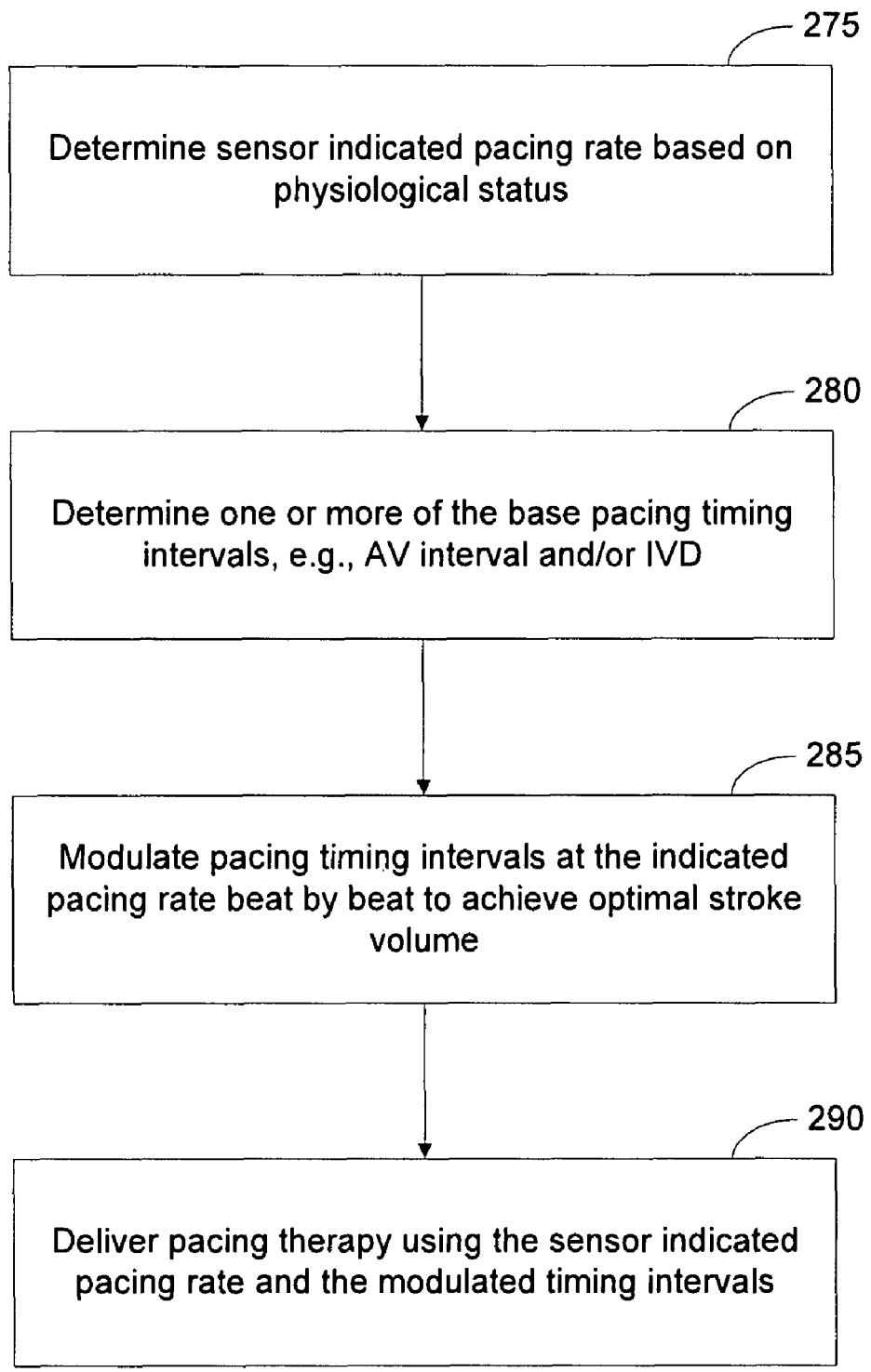
FIG. 2C is a flow diagram illustrates a method for beat-to-beat modulation of base timing intervals in accordance with embodiments of the invention.

The flow diagram of FIG. 2C illustrates a method for beat to beat modulation of pacing intervals in accordance with embodiments of the invention. A sensor indicated rate is determined 275 based on patient activity. One or more base pacing timing intervals are determined 280. For example, pacing timing intervals the AV interval and/or interventricular delay (IVD) may be determined which are indicated to provide therapy for the patient's particular dysfunction. These pacing timing intervals may be programmed into the device by a physician via a device programmer or may be determined by the device. The base pacing timing intervals may be updated through periodic testing track changes in the patient's condition. Once the base pacing timing intervals are determined, these timing intervals are modulated 285 to mimic the natural interval modulation that occurs as heart rate increases. In some embodiments, modulation to mimic the effects of RSA may also be performed. Therapy is delivered 290 using the indicated pacing rate and the modulated pacing timing intervals.

Modulation of the pacing timing intervals may be accomplished using inputs from various sensors to provide feedback control. For example, measurements of stroke volume, cardiac output, total peripheral resistance, pulmonary artery (PA) pressure, hemodynamics, blood flow, blood pressure (e.g., RV, LV, or arterial blood pressure), autonomic tone, baroreflex, chemoreflex, cardiac contractility measurements, and/or other physiological parameters may be used individually or together to control the pacing timing intervals of the next beat.

In one embodiment, an algorithm is implemented to generate intervals that help to promote or maintain autonomic tone. Autonomic tone can become unbalanced during heart disease with more sympathetic tone vs. parasympathetic tone. The algorithm to adjust pacing timing intervals based on autonomic tine may be accomplished by changing intervals until autonomic tone is improved and more balanced.

Baroreflex responds directly to changes in hemodynamics and may be used to modulate the pacing timing intervals to improve hemodynamics. Chemoreflex may respond to biomarkers such as B-type natriuretic peptide (BNP), atrial natriuretic peptide (ANP), matrix metalloproteinase (MMP), and/or inflammatory markers. Changes in these parameters may signal improving or worsening health status and may indicate changes in interval timing would be beneficial.

The parameters may be measured or derived from sensor signals produced by transthoracic impedance sensors, optical sensors, accelerometers, heart sound sensors, PA pressure sensors, RV, LV or arterial pressure sensors, posture sensors, and/or other sensor types. In some implementations, modulation of the timing intervals for a cardiac cycle is based on one or more parameter values, e.g., stroke volume, cardiac output, pressure and/or flow, measured just prior to the cardiac cycle. In other implementations, modulation of the timing intervals is based on a history of parameter measurements, e.g., chemoreflex and/or autonomic tone, taken over a relatively longer period of time prior to the cardiac cycle. Approaches for measuring stroke volume and cardiac output, aspects of which may be utilized in conjunction with the present invention, are described in commonly owned U.S. Pat. Nos. 4,674,518, 4,686,987, and 5,417,717 which are incorporated herein by reference.

Parameter measurements made during a cardiac beat may be used to control the pacing timing intervals of the next beat. For example, a right-sided sensed parameter is particularly useful for controlling pacing timing intervals for the next beat because the right ventricle is one beat ahead of the left ventricle during increases in venous blood return (preload). Thus, a right-sided sensed parameter, such as pulmonary artery (PA) pressure, may be used to provide data to control the timing intervals for the next paced beat.

Figure 3A:
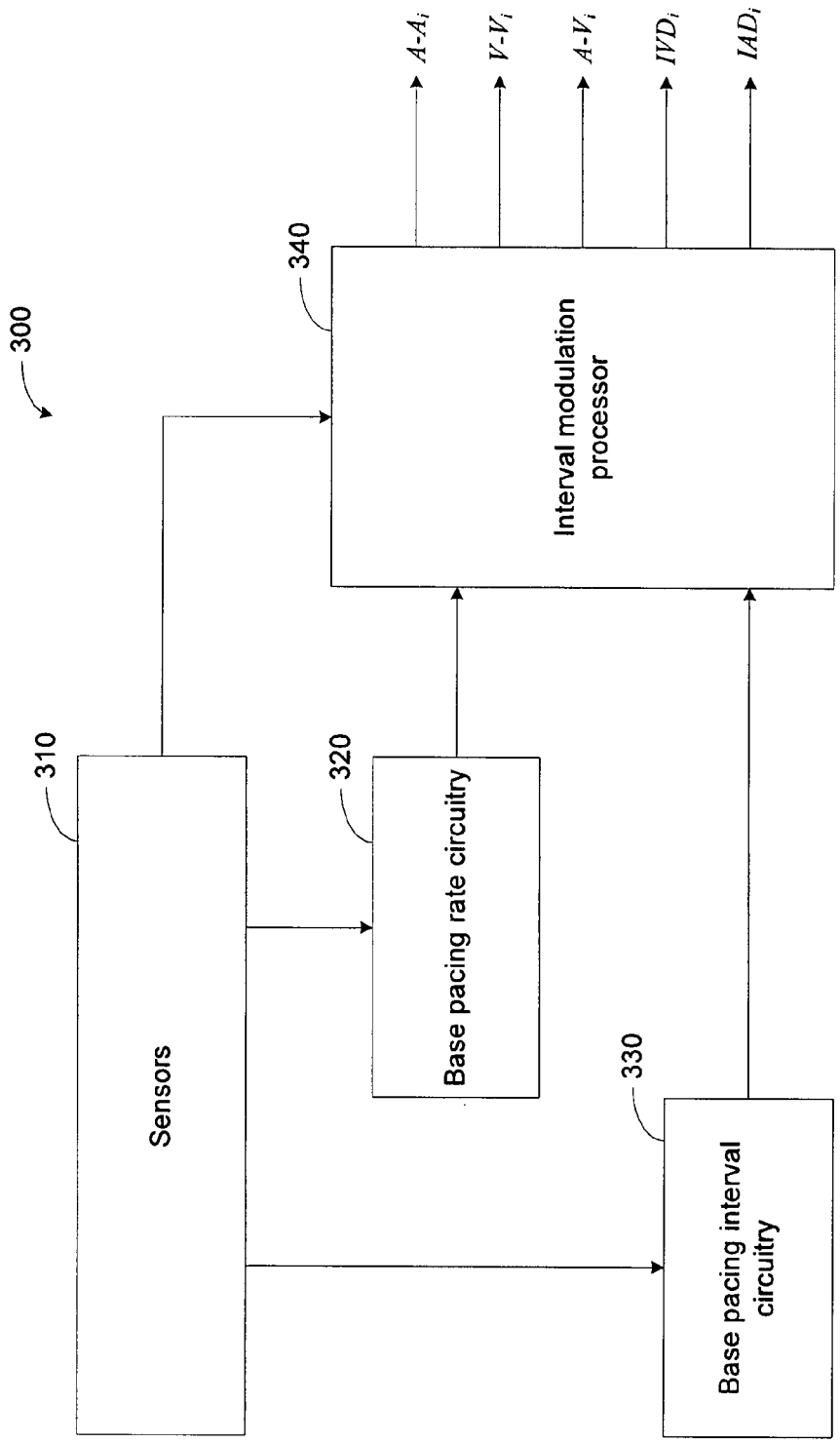
FIG. 3A is a block diagram of pacing interval modulation circuitry implementable in a cardiac rhythm management (CRM) device that may be used to determine rate dependent modulation of pacing timing intervals in accordance with embodiments of the invention.

FIG. 3A is a block diagram of pacing interval modulation circuitry 300 of a cardiac rhythm management (CRM) device that may be used to determine rate dependent modulation of pacing timing intervals in accordance with embodiments of the invention. The circuitry includes a sensing system having sensors 310 configured to sense physiologic parameters that are used to determine base pacing rate, base pacing timing intervals, and to control modulation of the pacing timing intervals. For example, in some implementations, an accelerometer may be used to provide a signal indicating patient activity level that is used by the pacing rate circuitry 320 to determine the SIR. A transthoracic impedance sensor may be used to generate a respiration signal from which respiration cycle phase may be determined. The pacing intervals may be modulated by the processor 340 based on the respiration cycle phase to produce pacing that mimics respiratory sinus arrhythmia.

Values of one or more of the pacing timing intervals, such as the base AV and/or IVD intervals, may be programmed into the CRM device and/or may be determined by the pacing interval circuitry 330 using the sensed parameters. Various techniques have been developed to determine pacing intervals to provide effective therapy for patients based on their particular pathology. For example, U.S. Pat. No. 7,181,285 describes processes for determining an A-V interval based on measured values of the intrinsic P-R intervals and determining an IVD interval based on the measured interval between right and left ventricular events. U.S. Pat. No. 5,334,222 describes a process for determining a A-V interval based on measures of cardiac function, including stroke volume and cardiac output which are assessed using measured intracardiac impedance variations due to the influx and outflow of blood from one of the ventricular chambers. U.S. Pat. No. 5,700,417 describes determining an A-V interval based on mechanical AV delay measured using heart sounds detected by an accelerometer. U.S. Pat. No. 6,371,922 describes determination of the A-V pacing interval based on baroreflex sensitivity measured using sensors for monitoring atrial and/or ventricular cycle length from an electrogram and pulse pressure. U.S. Pat. No. 6,371,922 describes determining cycle length from an electrogram signal and determining pulse pressure from Doppler echo, radial tonometry, plethsmography, or other techniques.

The interval modulation processor 340 receives the SIR (which may include RSA variation) calculated by the pacing rate circuitry 320. The interval modulation processor 340 also receives the base pacing timing intervals determined by the pacing interval circuitry 330. The SIR and base pacing timing intervals are modulated by the processor 340 to achieve modulation that provides optimal stroke volume for each cardiac cycle. Modulation of the SIR and the indicated pacing timing intervals is accomplished using one or more of the parameters sensed by the sensor system 310. The interval modulation processor 340 uses the parameters to modulate the timing intervals beat by beat.

In general, the modulated pacing timing intervals for cardiac cycle may be calculated using Equations [1-3].

$$AA_i = \text{CycleLength}_i + K_1 \cdot SP_{1i} + K_2 \cdot SP_{2i} + \ldots + K_M \cdot SP_{Mi} \quad [1]$$

$$VV_i = \text{CycleLength}_i + L_1 \cdot SP_{1i} + L_2 \cdot SP_{2i} + \ldots + L_M \cdot SP_{Mi} \quad [2]$$

$$\Delta AV_i = VV_i - AA_i \quad [3]$$

where $AA_i$ is the atrial pacing interval between atrial events of cardiac cycle i−1 and cardiac cycle i; $VV_i$ is the ventricular pacing interval between ventricular events of cardiac cycle i−1 and cardiac cycle i, and $\Delta AV_i$ is the change in the AV interval of cardiac cycle i−1 and cardiac cycle i. CycleLength$_i$ is the cycle length indicated by the SIR. Sensed parameters SP$_{1i}$, SP$_{2i}$, ... SP$_{Mi}$ are sensed parameters used to modulate the pacing timing intervals of cardiac cycle i. Modulation coefficients K$_1$, K$_2$, ... K$_M$ and L$_1$, L$_2$, ... L$_M$ are functions of the SIR. The modulation coefficients of Equations [1-3] can be determined using patient population data or can be individualized for a patient. The results produced by Equations [1-3] above can be improved by increasing the amount and quality of patient population data and/or individual data used to develop the coefficients.

The coefficients are related to the degree of modulation of the timing intervals and the relative weight given to various parameters in determining the modulation. As previously discussed, these coefficients may be individualized for a particular patient. For example, the device may change the degree of timing interval modulation or the weighting for a particular parameter over a period of time while monitoring patient responses, including, but not limited to activity response, autonomic tone, hemodynamic response, chemoreflex response, and/or baroreflex response. Using this information, selection of an appropriate degree of modulation, the parameters used to control the modulation, and/or the weight given to each parameter for the individual patient may be determined.

Figure 3B:
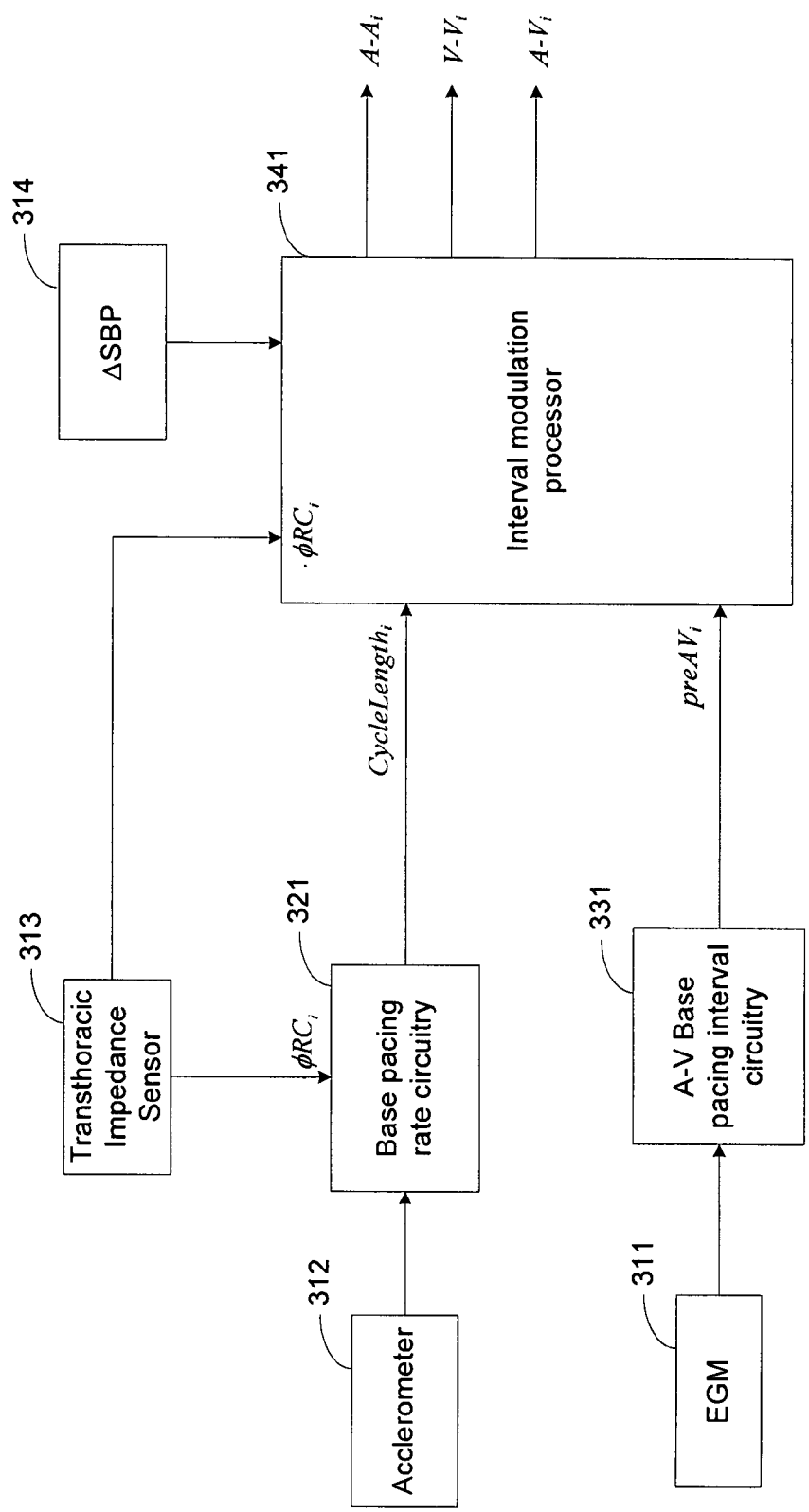
FIG. 3B is a block diagram of pacing interval modulation circuitry in accordance with embodiments of the invention.
Figure 4:
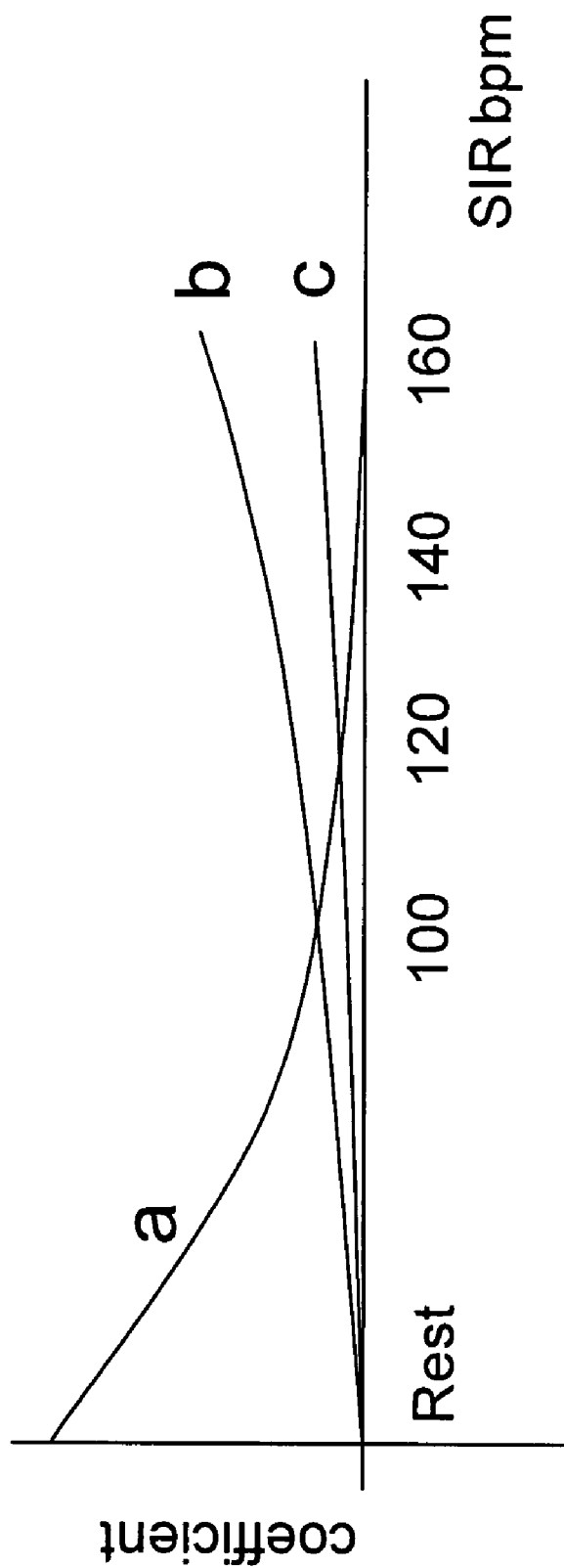
FIG. 4 illustrates representative graphs of pacing interval modulation coefficients in accordance with embodiments of the invention.

FIGS. 3B and 4 provide an example of the operation of the pacing interval modulation circuitry in accordance with an embodiment of the invention. In this embodiment, an accelerometer 312 is used to sense patient activity and a transthoracic impedance sensor 313 senses patient respiration. The patient activity signal from the accelerometer 312 is used by the pacing interval circuitry 321 to determine a SIR. The pacing interval circuitry outputs cycle length for cardiac cycle i, denoted CycleLength$_i$, based on the SIR. CycleLength$_i$ may also be varied for respiration cycle phase, •φRC$_i$, based on the respiration signal produced by the impedance sensor 313. An AV pacing interval (preAV$_i$) is initially determined by the pacing interval circuitry 331. In this embodiment, the preAV$_i$ pacing timing interval is calculated based on intrinsic P-R intervals measured from the cardiac electrical signals detected by a cardiac electrogram circuitry 311. The preAV$_i$ may be calculated to improve the patient's hemodynamic response, such as an optimized AV delay for CRT pacing.

The CycleLength$_i$, of the SIR and the preAV$_i$ pacing timing interval are input to the interval modulation processor 341. Respiration cycle phase for cardiac cycle i, denoted •φRC$_i$, is determined from the respiration signal generated by the transthoracic impedance sensor 313. The interval modulation processor 341 varies the modulation intervals of the SIR based on respiration cycle phase. Ventilation can change intrathoracic pressures affecting blood return and preload on the heart, causing changes in stroke volume. The pacing timing intervals may be modulated to compensate for these natural fluctuations in stroke volume. For example, the pacing interval modulation processor may modulate the timing intervals to deliver an appropriate A-V interval and HRV.

Additionally, the interval modulation processor 341 can modulate the pacing timing intervals of the SIR using the signal derived from a sensor 314 that indicates changes in systolic blood pressure (SBP). For example sensor 314 may comprise a pressure sensor that provides dP/dt or may comprise an accelerometer configured to sense heart sounds.

The level of the SIR may also be used to determine the level of modulation of the pacing intervals to achieve the rate based modulation described herein. For example, at rest, the pacing interval modulation may affect both the A-A and V-V intervals nearly equally. With increased exercise, A-A modulation decreases but remains present to some degree. As the heart rate increases, modulation in the A-A interval is nearly cancelled by modulation of the A-V interval to keep the V-V interval substantially constant.

For example, for the embodiment illustrated by FIG. 3B, the modulated pacing timing intervals for cardiac cycle may be calculated using Equations [4-6].

$$AA_i = \text{CycleLength}_i + a \cdot \phi RC_i + b \cdot \Delta SBP_i \quad [4]$$

$$VV_i = \text{CycleLength}_i + a \cdot RC_i + c \cdot \Delta SBP_i \quad [5]$$

$$\Delta AV_i = VV_i - AA_i \quad [6]$$

Modulation coefficients a, b, and c are a function of the SIR. Representative graphs of modulation coefficients a, b, and c are illustrated in FIG. 4. These graphs may be developed based on patient population data as previously discussed.

Figure 5:
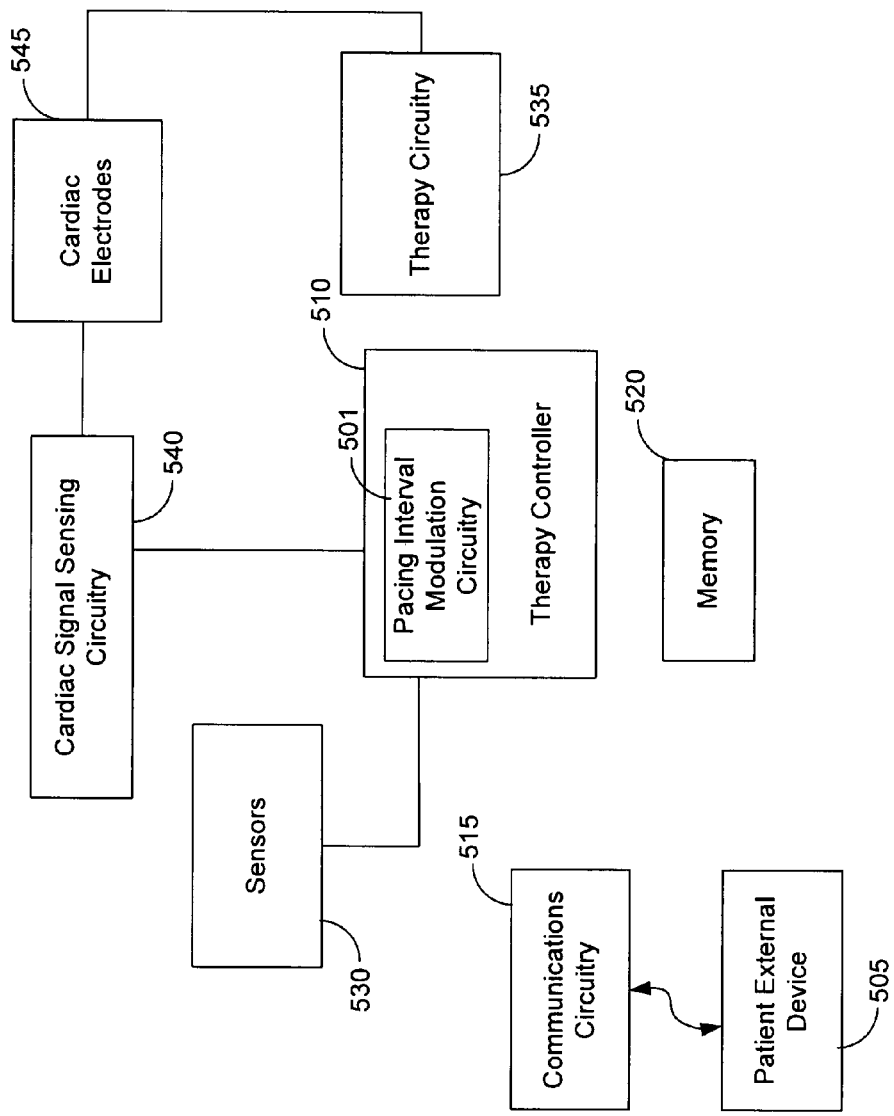
FIG. 5 is a block diagram of circuitry that may be used for implementing a pacing timing interval modulation in accordance with embodiments of the present invention.

FIG. 5 is a block diagram of a CRM device 500 including a therapy controller 510 incorporating pacing interval modulation circuitry 501 in accordance with embodiments of the invention. Cardiac electrode 545 may be positioned or disposed at multiple locations within a heart chamber or vasculature.

One or more sensors 530 are configured to sense physiological parameters used to determine a SIR, detect respiration cycle phase, determine an initial AV interval and provide rate based modulation of the pacing timing intervals as discussed above. Useful sensors 530 include a sensor or sensors that detect heart sounds (e.g., microphone, accelerometer), a pressure sensor (e.g., left arterial pressure sensor such as a pulmonary artery pressure sensor, right ventricular pressure sensor), and a cardiac stroke impedance sensor, optical fiber sensor configured to sense stroke and/or respiration among other sensor types. Signals produced by the one or more sensors 530 may be communicated to a pacing therapy controller 510 which includes circuitry 501 for modulating the pacing timing intervals.

Additionally, the therapy controller 510 and the therapy circuitry 535 may include functionality to modulate myocardial contractility. Changes in stroke volume can be produced by changes in ventricular contractility. Patients suffering from heart failure experience decreased cardiac contractility that causes a reduction in stroke volume as well as an increase in preload. The increased preload may lead to pulmonary congestion and edema. Non-excitory electrical stimulation may be used to increase contractility during periods of increased preload. Stimulation to increase contractility may be combined with increased A-V paced intervals in situations with increased afterload.

The therapy controller 510 is coupled to the sensors 530, memory 520, cardiac signal sensing circuitry 540, and therapy circuitry 535. The memory 520 is configured to store program instructions and/or data. In addition, the stored information may be used to provide a log of events for display or analysis at a later time. The memory 520 may be configured to store program instructions that execute algorithms to implement modulation of pacing timing intervals. Pacing timing interval modulation circuitry 501 executes the program instructions to implement timing interval modulation in accordance with embodiments of the present invention.

The therapy controller 510 is preferably coupled to communications circuitry 515 which allows the device to communicate with patient external devices 505, such as a patient-external programmer or advanced patient management system. In some implementations, an advanced patient management (APM) system may be used to collect patient data for purposes of developing patient population data from which coefficients of the timing interval modulation algorithm may be determined. This data may be acquired from numerous patients. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 6:
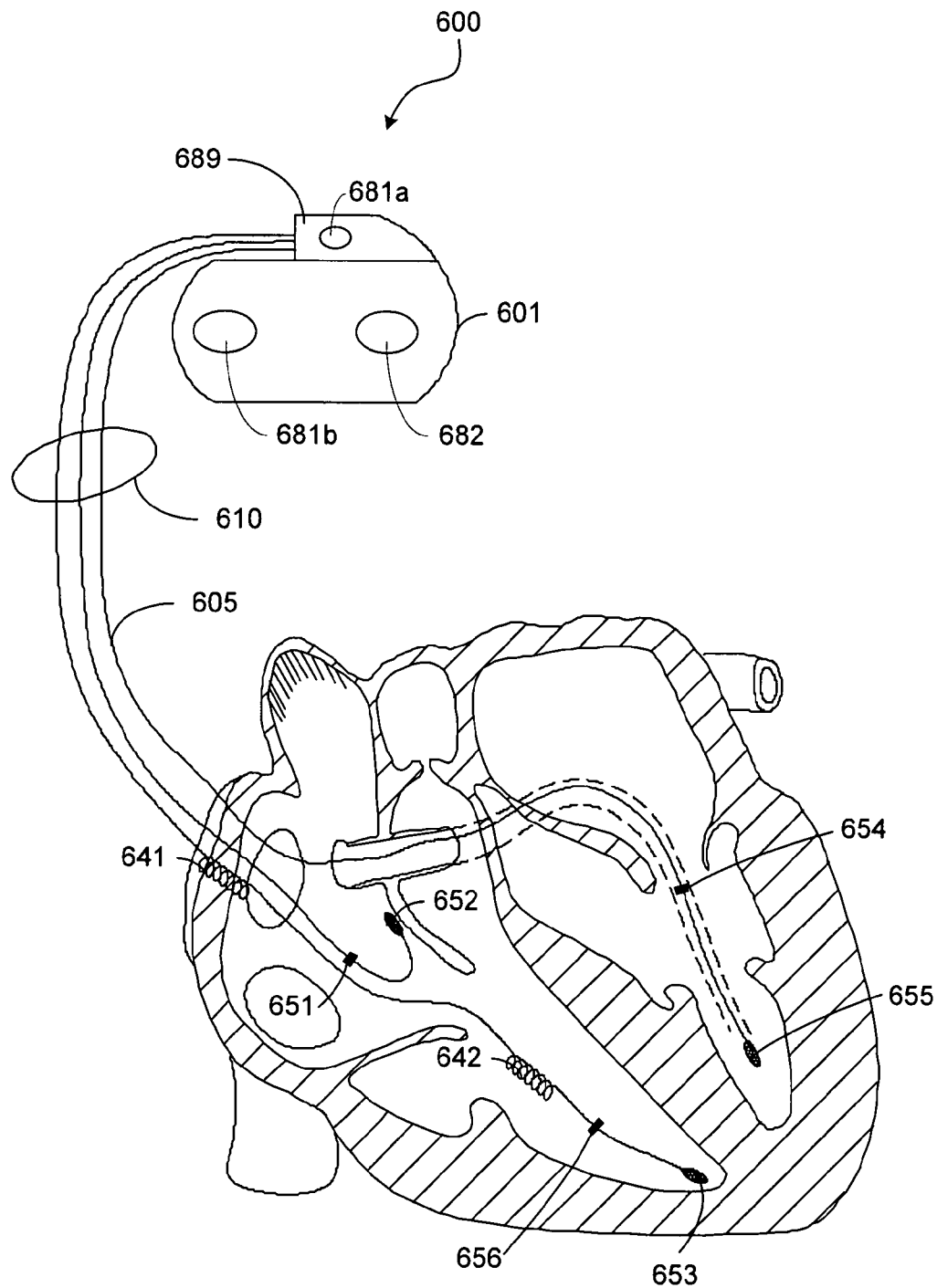
FIG. 6 illustrates a patient-implantable device that may be used in conjunction with a pacing timing interval modulation in accordance with embodiments of the present invention.

FIG. 6 shows an embodiment of the present invention implemented with use of an implanted cardiac therapy device 600. The therapy device 600 includes cardiac rhythm management circuitry enclosed within an implantable housing 601. The CRM circuitry is electrically coupled to an intracardiac lead system 610. Portions of the intracardiac lead system 610 are shown inserted into the patient's heart. The lead system 610 includes cardiac pace/sense electrodes 651-656 positioned in, on, or about one or more heart chambers for sensing electrical signals from the patient's heart and/or delivering pacing pulses to the heart. The intracardiac sense/pace electrodes 651-656 may be used to sense and/or pace one or more chambers of the heart, including the left ventricle, the right ventricle, the left atrium and/or the right atrium. The lead system 610 may include one or more defibrillation electrodes 641, 642 for delivering defibrillation/cardioversion shocks to the heart.

Portions of the housing 601 of the implantable device 600 may optionally serve as one or multiple can or indifferent electrodes. The housing 601 is illustrated as incorporating a header 689 that may be configured to facilitate removable attachment between one or more leads and the housing 601. The housing 601 of the therapy device 600 may include one or more can electrodes 681b. The header 689 of the therapy device 600 may include one or more indifferent electrodes 681a.

The housing 601 and/or header 689 may include one or more sensors 682, such as an accelerometer or microphone. One or more cardiac leads 610 or separate sensor leads may incorporate one or more sensors, such as a pulmonary arterial pressure sensor. The cardiac electrodes and/or other sensors disposed within or on the housing 601 or lead system 610 of the therapy device 600 may produce signals used for detection and/or measurement of various physiological parameters, such as transthoracic impedance, respiration rate, minute ventilation, heart rate, cardiac dysynchrony, activity, posture, blood chemistry, O2 saturation, heart sounds, wall stress, wall strain, hypertrophy, inter-electrode impedance, electrical delays (PR interval, AV interval, QRS width, etc.), cardiac chamber pressure, cardiac output, temperature, respiration sinus arrhythmia, heart rate variability, depolarization amplitudes, depolarization timing, and/or other physiological parameters. It is contemplated that, in certain embodiments, information derived from such signals may be incorporated into the algorithm that is employed to determine modulated pacing timing intervals for pacing therapy.

In some configurations, the implantable device 600 may incorporate one or more transthoracic impedance sensors that may be used to acquire the patient's respiratory waveform, and/or to acquire other respiratory-related information. The transthoracic impedance sensor may include, for example, one or more intracardiac electrodes 641, 642, 651-656 positioned in one or more chambers of the heart. The intracardiac electrodes 641, 642, 651-656 may be coupled to impedance drive/sense circuitry positioned within the housing 601 of the therapy device 600. Information from the transthoracic impedance sensor may be used to determine an SIR to correspond to the patient's activity or metabolic need and/or may be used to modulate the pacing rate and/or pacing intervals with respiration cycle phase, among other uses.

Communications circuitry is disposed within the housing 601 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 600 may include circuitry for detecting and treating cardiac tachyarrhythmia via defibrillation therapy and/or anti-tachyarrhythmia pacing (ATP). Configurations providing defibrillation capability may make use of defibrillation coils 641, 642 for delivering high energy shocks to the heart to terminate or mitigate tachyarrhythmia.

In some embodiments, the implantable therapy device 600 may include circuitry for selection of pacing electrode(s), timing sequence, and/or amplitude or pulse waveform output configurations (collectively referred to as pacing output configuration) to be applied via one or multiple electrodes within one or multiple heart chambers. The implantable therapy device 600 may include functionality to deliverer non-excitory electrical stimulation via one or more electrodes. In a pacemaker equipped with multiple pacing electrodes respectively disposed at multiple pacing sites within a heart chamber, the ability to select one or more electrodes, temporal sequence, and/or pulse waveform characteristics for delivery of pacing can be used enhance the contractile function of the heart chamber.

Multi-site pacemakers are capable of delivering electrical stimulation to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, anodal/cathodal polarity and/or waveshape of the pacing pulses may also be altered to enhance pumping function.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac rhythm management device, comprising:
a sensor system including one or more sensors configured to sense one or more physiological parameters;
a therapy control processor configured to adjust, for each cardiac cycle, an atrioventricular (A-V) timing interval to decrease beat-to-beat ventricular (V-V) variability over a plurality of cardiac cycles based on the sensed physiological parameters so as to maintain relatively constant V-V intervals between ventricular beats of different cardiac cycles over the plurality of cardiac cycles; and a therapy delivery system configured to deliver pacing to a heart using the adjusted A-V timing interval.

2. The device of claim 1, wherein:
the sensor system includes a respiration sensor; and
the therapy control processor is configured to determine a respiration cycle phase and to adjust the A-V timing interval based on the respiration cycle phase.

3. The device of claim 1, wherein:
the therapy control processor is configured to control delivery of non-excitatory electrical stimulation to alter myocardial contractility; and
the therapy delivery system is configured to deliver the non-excitatory electrical stimulation under control of the therapy control processor.

4. The device of claim 1, wherein the therapy control processor is further configured to adjust one or more of an interventricular timing interval, an intraventricular timing interval, an interatrial timing interval, and an intraatrial timing interval.

5. The device of claim 1 wherein:
the sensor system is configured to sense a physiological parameter of a right heart chamber during a cardiac cycle; and
the therapy control processor is configured to independently adjust the A-V timing interval for a next cardiac cycle based on the sensed physiological parameter.

6. The device of claim 1, wherein the therapy control processor is configured to provide rate dependent adjustment of the A-V timing interval to produce optimal stroke volume for each cardiac beat.

7. The device of claim 1, wherein the therapy control processor is further configured to determine an indicated pacing rate based on the one or more physiological parameters.

8. The device of claim 7, wherein the therapy control processor is further configured to determine the indicated pacing rate based on one or more of metabolic need, autonomic tone, and hemodynamic status.

9. The device of claim 1, wherein the pacing delivered by the therapy delivery system provides heart failure therapy, and wherein the therapy control processor is further configured to independently adjust at least one pacing interval to optimize the heart failure therapy.

10. The device of claim 1, wherein the therapy control processor is further configured to independently adjust the A-V timing interval based on one or more of blood pressure, blood flow, baroreflex, and chemoreflex.

11. The device of claim 1, wherein the therapy control processor is further configured to independently adjust the A-V timing interval based on cardiac contractility.

12. A cardiac rhythm management device, comprising:
a sensor system including sensors configured to sense one or more physiological parameters;
pacing rate circuitry configured to determine an indicated pacing rate based on the sensed one or more physiological parameters and to vary the indicated pacing rate to mimic natural respiratory sinus arrhythmia;
a therapy control processor configured to independently adjust, for each cardiac cycle, an atrioventricular (A-V) timing interval to decrease beat-to-beat ventricular (V-V) variability over a plurality of cardiac cycles based on the sensed physiological parameters so as to maintain relatively constant V-V intervals between ventricular beats of different cardiac cycles over the plurality of cardiac cycles; and
a therapy delivery system configured to deliver pacing to a heart using the adjusted A-V timing interval.

13. The device of claim 12, wherein:
the sensor system includes a sensor configured to sense a parameter indicative of autonomic tone; and
the therapy control processor is configured to adjust the A-V timing interval based on autonomic tone.

14. The device of claim 12, wherein:
the therapy control processor is configured to control delivery of non-excitatory electrical stimulation to alter myocardial contractility; and
the therapy delivery system is configured to deliver the non-excitatory electrical stimulation under control of the therapy control processor.

15. The device of claim 12, wherein the therapy control processor is further configured to adjust one or more of an interventricular timing interval, an intraventricular timing interval, an interatrial timing interval, and an intraatrial timing interval.

16. The device of claim 12 wherein:
the sensor system is configured to sense a physiological parameter of a right heart chamber during a cardiac cycle; and
the therapy control processor is configured to independently adjust the A-V timing interval of the indicated pacing rate for a next cardiac cycle based on the sensed right heart chamber parameter.

17. The device of claim 12, wherein the therapy control processor is configured to provide rate dependent adjustment of the A-V timing interval to produce optimal stroke volume for each cardiac beat.

18. The device of claim 12, wherein:
the sensor system includes a sensor configured to sense pulmonary artery pressure; and
the therapy control processor is configured to adjust the A-V timing interval based on pulmonary artery pressure.

* * * * *